US012564666B2

(12) United States Patent
Hermann et al.

(10) Patent No.: US 12,564,666 B2
(45) Date of Patent: Mar. 3, 2026

(54) METHOD FOR TEMPORARILY INTERRUPTING AN EXTRACORPOREAL BLOOD TREATMENT, CONTROL DEVICE AND BLOOD TREATMENT APPARATUS

(71) Applicant: Fresenius Medical Care Deutschland GmbH, Bad Homburg (DE)

(72) Inventors: Uwe Hermann, Nuthetal (DE); Sabine Kipp, Bad Homburg (DE); Christine Nachbaur-Sturm, Hofheim a. Ts. (DE); Thomas Pusinelli, Altenstadt (DE); Martin Gruendken, Rosbach (DE); Georg Verch, Wiesbaden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 18/410,649

(22) Filed: Jan. 11, 2024

(65) Prior Publication Data

US 2024/0139397 A1 May 2, 2024

Related U.S. Application Data

(63) Continuation of application No. 15/628,210, filed on Jun. 20, 2017, now Pat. No. 11,918,724, which is a
(Continued)

(30) Foreign Application Priority Data

| | | |
|---|---|---|
| Nov. 24, 2009 | (DE) | ......................... 102009054415.1 |
| Mar. 10, 2010 | (DE) | ......................... 102010010928.2 |

(51) Int. Cl.
| | |
|---|---|
| *A61M 1/16* | (2006.01) |
| *A61M 1/36* | (2006.01) |
(Continued)

(52) U.S. Cl.
CPC ........ *A61M 1/3653* (2013.01); *A61M 1/3656* (2014.02); *A61M 60/113* (2021.01);
(Continued)

(58) Field of Classification Search
CPC .. A61M 1/365; A61M 1/152; A61M 1/15632; A61M 1/1694; A61M 1/36222;
(Continued)

(56) References Cited

U.S. PATENT DOCUMENTS

| | | |
|---|---|---|
| 5,591,344 A | 1/1997 | Kenley et al. |
| 5,650,071 A | 7/1997 | Brugger et al. |
(Continued)

FOREIGN PATENT DOCUMENTS

| | | |
|---|---|---|
| CN | 1356915 | 7/2002 |
| CN | 1946440 | 4/2007 |
(Continued)

OTHER PUBLICATIONS

[No Author Listed], "Dialysegerät Dialog," B. Braun, May 2007, 276 pages (with English translation of relevant pages).
(Continued)

*Primary Examiner* — Kai H Weng
(74) *Attorney, Agent, or Firm* — Fish & Richardson P.C.

(57) ABSTRACT

The present invention relates to a method for temporarily interrupting an extracorporeal treatment of blood of a patient by use of a blood treatment apparatus. The method comprises activating or controlling a control device provided and configured to bring the blood treatment apparatus into a state in which the blood treatment session of the patient can be interrupted with the intention to continue the blood treatment session. The present invention further relates to a control device, a blood treatment apparatus, a digital storage means, a computer program product as well as a computer program.

20 Claims, 2 Drawing Sheets

Related U.S. Application Data continuation of application No. 13/511,288, filed as application No. PCT/EP2010/007074 on Nov. 23, 2010, now Pat. No. 9,713,670.

(51) Int. Cl.

| | |
|---|---|
| *A61M 60/113* | (2021.01) |
| *A61M 60/279* | (2021.01) |
| *A61M 60/37* | (2021.01) |
| *A61M 60/38* | (2021.01) |
| *A61M 60/538* | (2021.01) |
| *A61M 60/546* | (2021.01) |
| *A61M 60/554* | (2021.01) |
| *A61M 60/585* | (2021.01) |
| *A61M 60/847* | (2021.01) |
| *A61M 60/849* | (2021.01) |
| *A61M 1/30* | (2006.01) |
| *A61M 1/34* | (2006.01) |

(52) U.S. Cl.
  CPC .......... *A61M 60/279* (2021.01); *A61M 60/37* (2021.01); *A61M 60/38* (2021.01); *A61M 60/538* (2021.01); *A61M 60/546* (2021.01); *A61M 60/554* (2021.01); *A61M 60/585* (2021.01); *A61M 60/847* (2021.01); *A61M 60/849* (2021.01); *A61M 1/1601* (2014.02); *A61M 1/1605* (2014.02); *A61M 1/30* (2013.01); *A61M 1/305* (2014.02); *A61M 1/34* (2013.01); *A61M 1/3424* (2014.02); *A61M 1/36* (2013.01); *A61M 1/3643* (2013.01); *A61M 1/3644* (2014.02); *A61M 1/3646* (2014.02); *A61M 1/3675* (2013.01); *A61M 2205/3306* (2013.01); *A61M 2205/50* (2013.01); *A61M 2205/502* (2013.01); *Y10T 137/0324* (2015.04)

(58) Field of Classification Search
  CPC ........ A61M 1/36225; A61M 1/362265; A61M 1/3627; A61M 1/3646; A61M 1/3653; A61M 1/154; A61M 1/36224; A61M 1/362262; A61M 1/16; A61M 1/168; A61M 1/3647; A61M 1/3649
  See application file for complete search history.

(56) References Cited

U.S. PATENT DOCUMENTS

| | | | |
|---|---|---|---|
| 5,776,345 | A | 7/1998 | Truitt et al. |
| 6,947,131 | B2 | 9/2005 | O'Mahony et al. |
| 8,523,799 | B2 | 9/2013 | Biesel et al. |
| 8,991,414 | B2 | 3/2015 | Gronau et al. |
| 2001/0007058 | A1 | 7/2001 | Jonsson et al. |
| 2001/0048892 | A1 | 12/2001 | Bainbridge et al. |
| 2002/0004530 | A1 | 1/2002 | Warnock |
| 2003/0100857 | A1 | 5/2003 | Pedrazzi et al. |
| 2003/0232093 | A1 | 12/2003 | Faict et al. |
| 2004/0088189 | A1 | 5/2004 | Veome et al. |
| 2005/0209546 | A1 | 9/2005 | Jonsson et al. |
| 2007/0158247 | A1 | 7/2007 | Carr et al. |
| 2007/0239096 | A1 | 10/2007 | Keenan et al. |
| 2008/0027368 | A1 | 1/2008 | Kollar et al. |
| 2009/0043240 | A1 | 2/2009 | Robinson et al. |
| 2009/0076433 | A1 | 3/2009 | Folden et al. |
| 2009/0114593 | A1 | 5/2009 | Fischer |
| 2009/0160656 | A1 | 6/2009 | Seetharaman et al. |
| 2010/0121246 | A1 | 5/2010 | Peters et al. |
| 2010/0192686 | A1 | 8/2010 | Kamen et al. |

FOREIGN PATENT DOCUMENTS

| | | |
|---|---|---|
| DE | 10011208 | 9/2001 |
| DE | 102006022122 | 11/2007 |
| DE | 102006061184 | 6/2008 |
| DE | 102009008346 | 8/2010 |
| EP | 1595560 | 11/2005 |
| EP | 1736185 | 12/2006 |
| EP | 1837046 | 9/2007 |
| JP | H06-014993 | 1/1994 |
| JP | H06-014995 | 1/1994 |
| JP | H08-38597 | 2/1996 |
| JP | H09-511605 | 11/1997 |
| JP | H11-226121 | 8/1999 |
| JP | 2001-054571 | 2/2001 |
| JP | 2003-517892 | 6/2003 |
| JP | 2003-180825 | 7/2003 |
| JP | 2004-097782 | 4/2004 |
| JP | 2004-144080 | 5/2004 |
| JP | 2004-222884 | 8/2004 |
| JP | 2005-103043 | 4/2005 |
| JP | 2006-505349 | 2/2006 |
| JP | 2006-280775 | 10/2006 |
| JP | 2007-000621 | 1/2007 |
| JP | 2007-044065 | 2/2007 |
| JP | 2007-090058 | 4/2007 |
| JP | 2008-043475 | 2/2008 |
| JP | 2008-062089 | 3/2008 |
| WO | WO 01/45767 | 6/2001 |
| WO | WO 01/51106 | 7/2001 |
| WO | WO 03/002174 | 1/2003 |
| WO | WO 2006/073166 | 7/2006 |
| WO | WO 2009/109351 | 9/2009 |
| WO | WO 2011/063923 | 6/2011 |

OTHER PUBLICATIONS

[No Author Listed], "Guidance for procedure of chronic extracorporeal dialysis—Quality management in dialysis units," DIN VDE 0753-4, Jan. 2006, 57 pages (with English translation of relevant pages).
[No Author Listed], "Guideline for the safe use of medical products in dialysis treatment—Introduction," DIN VDE 0753-4, May 2009, 5 pages (with English translation).
[No Author Listed], "Guideline for the safe use of medical products in dialysis treatment," DIN VDE 0753-4, May 2009, 57 pages (with English translation).
[No Author Listed], "Technische Information," B. Braun, Nov. 2008, 53 pages (with English translation of relevant p. 7).
Affidavit of Dr. Kai von Appen, signed Aug. 12, 2015, 8 pages (with English translation).
Affidavit of Dr. Stefan Mees, signed Aug. 12, 2015, 6 pages (with English translation).
Affidavit signed by Specialist Nurse Carina Jonsson regarding avaibility of Prismaflex, dated Mar. 11, 2021, 1 page.
Breuch, "Auszug aus Fachpflege Neuphrologie und Dialyse," Urban and Fischer, 2000, 171-176, 193-194, 16 pages (with English translation of relevant pages).
Gambro Lundia AB, "Operator's Manual: Software version 3.2x", Prismaflex, Feb. 2008, 245 pages.
PCT International Preliminary Report on Patentability in International Appln. No. PCT/EP2010/007074, mailed Jun. 7, 2012, 16 pages (with English translation).
PCT International Search Report from PCT/EP2010/007074, mailed on Feb. 17, 2011.
Q&A for quick understanding of ME6, Hemodialysis, Hemofiltration, Hemoperfusion; General Editor: Sakurai, Y., 4$^{th}$ Edition (Mar. 1, 1998), p. 63 (machine translation).

METHOD FOR TEMPORARILY INTERRUPTING AN EXTRACORPOREAL BLOOD TREATMENT, CONTROL DEVICE AND BLOOD TREATMENT APPARATUS

CROSS REFERENCE TO RELATED APPLICATIONS

This application is a continuation application of U.S. patent application Ser. No. 15/628,210, filed on Jun. 20, 2017, which is a continuation application Ser. No. 13/511, 288, filed on Jun. 18, 2012, now U.S. Pat. No. 9,713,670, which is a 371 national phase application of PCT/EP2010/007074 filed Nov. 23, 2010, which claims priority from German Patent Application No. DE 10 2009 054 415.1, filed Nov. 24, 2009 and German Patent Application No. DE 10 2010 010 928.2, filed Mar. 10, 2010.

TECHNICAL FIELD OF THE INVENTION

The present invention relates to a method for temporarily interrupting an extracorporeal blood treatment. The present invention further relates to a control device, a blood treatment apparatus, a digital storage means, a computer program product, and a computer program.

BACKGROUND OF THE INVENTION

Temporary or transient interruptions of extracorporeal blood treatment can be necessary for different reasons. Among these reasons are the application or placement of a new access to the blood vessel, the performance of medical examinations, a bathroom visit of the patient, etc. They all have in common that the extracorporeal blood treatment is intended to be continued after the reason for the temporary interruption has ceased to exist.

One object of the present invention is to propose a further method for temporarily interrupting an extracorporeal blood treatment. Furthermore, appropriate apparatuses are proposed.

According to the present invention, a method for temporarily interrupting an extracorporeal blood treatment of a patient or an extracorporeal treatment of the blood of the patient by means of a blood treatment apparatus to which the patient is connected for the purpose of the blood treatment is proposed. The method comprises the activation or control of a control device provided and configured to bring the blood treatment apparatus into a state in which the blood treatment session can be interrupted temporarily by means of disconnecting the patient from the blood treatment apparatus with the intention to continue the blood treatment session.

The terms "temporary interruption" or "temporarily interrupting" as used herein designate a temporally limited interruption of the method. The time span or the time period, respectively, of the interruption can be determined or set arbitrarily or variably, respectively. A mean interruption period can last between 0.5 h and 4 h. However, also a few minutes or more than 4 h can be encompassed by the term "temporary".

The temporary interruption can be performed with the intention to continue the interrupted session of the extracorporeal blood treatment. It can be performed with the intention to temporarily disconnect the patient and/or to bring the patient or the blood treatment apparatus into a disconnected state. The disconnection can be, but does not have to be, part of the method procedure.

According to the present invention, the terms "temporary" or "temporarily" can therefore be understood such that—in the moment of the interruption—there is the intention to continue the treatment at a later point of time, independently of whether this will actually happen or not.

In certain embodiments of the present invention temporary interruption is performed with the intention to continue the interrupted session of the extracorporeal blood treatment by means of at least one (or more or all) of the medical devices, which already had been used before the interruption of the blood treatment session. That way it can be advantageously omitted to discard one, more or all of the medical devices used or parts thereof before the end of the treatment. Additionally, the (complete or partial) dismantling or removal and—at the end of the interruption—setup of the blood treatment apparatus with new or unused, respectively, or sterilized medical devices, which takes time and effort, can be advantageously omitted. In some embodiments of the present invention in the moment of the interruption it is already planned or intended to reuse the medical device which had been used before the interruption for the continued treatment.

"Medical device" as used herein includes in some embodiments of the present invention blood lines, blood tubing sets, blood cassettes, trays, organizers and the like. Optionally they are designed, configured as disposables or used that way.

The term "extracorporeal blood treatment" as used herein refers to a blood treatment which is performed or carried out, respectively, outside a patient's body. Such a blood treatment can, for example, serve for purifying and/or replacing the blood of a patient.

The extracorporeal blood treatment can be performed by means of an extracorporeal blood circuit. The extracorporeal blood circuit can comprise a tube system or a patient tube system, respectively. The patient tube system can comprise a blood withdrawal line and a blood return line.

The term "blood withdrawal line" as used herein refers to a line or a line segment or line section of the extracorporeal blood circuit which is provided for conveying or conducting or transferring blood out of the patient or from the patient's blood circuit (or circulation, respectively).

The term "blood return line" as used herein refers to a line or a line segment or line section of the extracorporeal blood circuit which is provided for supplying or returning blood to the patient or to the patient's blood circuit, respectively.

The blood withdrawal line can, for example, be an arterial line or an arterial line section or segment of the extracorporeal blood circuit. The term "arterial line or arterial line section or segment" hereby refers to a part of the extracorporeal blood circuit which is connected to an artery of the patient's blood circuit or circulation.

With the blood withdrawal line being an arterial line section or segment of the extracorporeal blood circuit, the blood return line can correspondingly be a venous line or a venous line section or segment of the extracorporeal blood circuit, respectively. The term "venous line or venous line section or segment, respectively" correspondingly refers to a part of the extracorporeal blood circuit which is connected to a vein of the patient's blood circuit.

In other embodiments according to the present invention, the blood withdrawal line can be a venous line section or segment of the extracorporeal blood circuit and the blood return line can correspondingly be an arterial line section or segment. The latter is, inter alia, usually the case upon enriching blood with oxygen.

The patient tube system can comprise patient tube clamps which are provided for interrupting or terminating, respectively, a blood flow or blood stream inside an interior (line interior) of the blood withdrawal line and/or of the blood return line after having been closed or by means of the closure thereof, respectively. Accordingly, after having opened or by means of opening the corresponding patient tube clamp, respectively, it can be intended to continue the blood flow or the blood stream inside the line interior of the blood withdrawal line and/or the blood return line.

At least two patient tube clamps can be provided in the extracorporeal blood circuit; for example, at least one patient tube clamp can be provided in or at the blood withdrawal line, respectively, and at least one further patient tube clamp can be provided in or at the blood return line, respectively.

The term "patient" as used herein refers to a subject like a human or an animal independently of being healthy or ill.

A "blood treatment apparatus" encompasses apparatuses for performing a blood treatment such as a blood purification, for example, dialysis, hemofiltration, hemodiafiltration, apheresis, oxygenation (e.g., a method of introducing oxygen into blood), adsorption, or the like.

The term "control device" as used herein refers to a device which is designed, configured and/or provided for functionally interacting with the blood treatment apparatus in order to induce or effect an interruption of the extracorporeal blood treatment—optionally in addition to other effects.

The control device can be designed to enable an automation or an automatic or automated performance, respectively, of the method according to the present invention.

This can advantageously contribute to a reduction of the effort necessary for interrupting the blood treatment.

The control device can induce or effect the performance of all or substantially all method steps. The method according to the present invention can be performed substantially or completely by means of the control device. It can be performed partly or entirely by means of the control device.

In a preferred embodiment, the control device is activated or controlled in order to induce or effect a blood return of the blood present in the extracorporeal blood tube set (blood tube set, blood cassette, disposable) to the patient for the purpose of temporarily interrupting the blood treatment.

Alternatively or additionally, the control device can interrupt the blood treatment session without returning blood to the patient.

In a preferred embodiment, the control device is activated or controlled by means of actuating only one actuation device in order to bring the blood treatment apparatus into a state in which the blood treatment session of the patient can be interrupted or is interrupted with the intention to continue the blood treatment session or in which state the patient can be disconnected without having to take any further means—in particular at or on the blood treatment apparatus.

In a preferred embodiment, the control device is activated or controlled by a single or one-time actuating—such as, e.g., one key stroke, one movement of a controller or the like—of only one actuation device in order to bring the blood treatment apparatus into such a state in which the blood treatment session of the patient can be interrupted temporarily with the intention to continue the blood treatment session.

The actuation or activation or control of the control device can be effected by means of pushing, rotating, switching, etc., the actuation device.

Suitable actuation devices include a knob, a key, a soft key, a hard key, a switch, a controller, a button of a touch pad, a button of a touch screen, a button which can be actuated or activated by means of an external input device like a keypad, a mouse, a pen and the like, a speech input device and the like.

The control device can be activated or actuated by a user as, for example, clinic staff, e.g., physicians, nursing staff, the patient (e.g., in the case of a home dialysis) and the like.

The control device can be activated via signal transmission by means of another device.

By means of activating or controlling the control device, a background process assisting the user in the different stages of the blood treatment interruption can be initiated automatically.

Along with each single step of the blood treatment interruption messages can be output.

Such messages can require the affirmation of a user.

The messages can inform the user about the next operation steps.

In this way, it can advantageously be possible to allow a specific supervision or monitoring of the method according to the present invention by the user.

The method can comprise the initiation of the blood return with the control device inducing or effecting at least one of the following processes: disconnecting the blood withdrawal line of the extracorporeal blood circuit from the patient's blood circuit; starting the blood pump and/or opening the patient tube clamps of the blood withdrawal line and of the blood return line of the extracorporeal blood circuit.

The terms "effecting" or "inducing" as used herein mean that the control device is provided and configured to perform a process by itself.

The control device can be provided or configured to indicate, for example, by means of visual and/or acoustic notifications, that a process has to take place. For example, the control device can request a user to perform a manual process.

The term "blood return" as used herein refers to a method step or a process in which extracorporeally treated blood (as a whole or in parts thereof) of the patient which is, for example, present inside an extracorporeal blood circuit, will be reinfused into a patient's blood circuit.

The blood volume reinfused into the patient's blood circuit during a blood return can hereby, for example, amount to between 0 and 300 ml. A reinfusing process can be continued or repeated until a detection device provided in the extracorporeal blood circuit, such as, for example, an optical detector, detects or determines, respectively, an optical density "OD bright", the value of which can, for example, be predetermined and which can be used to conclude the absence of blood and/or the substantially exclusive presence of substituate liquid. For example, the reinfusion of 30 ml—once or to start with—can be continued. This volume can correspond to the residual blood volume in the venous line section or segment. Further blood can be reinfused. The reinfusion can subsequently be terminated.

A suitable method for the blood return can be found in the application of the present applicant having the title "Method for removing blood from an extracorporeal blood circuit for a blood treatment apparatus following termination of a blood treatment session and apparatus for performing such a method" which was filed at the German Patent and Trademark Office on Feb. 11, 2009 and which has the application number 10 2009 008 346.4 , the content of which is herewith fully incorporated by way of reference.

The terms "disconnecting" or "disconnection" as used herein refer to disconnecting the patient from an extracorporeal blood circuit. This can, for example, include the detachment or separation of a connection or of an access, respectively, such as, for example, a catheter, a shunt, a fistula, a cannula, a needle (e.g., in case of a veno-venous connection) and the like, between the blood circuit of the patient and the extracorporeal blood circuit.

A "disconnection of the blood withdrawal line of the extracorporeal blood circuit from the blood circuit of the patient" can thereby include closing a patient tube clamp of the blood withdrawal line and/or loosening or detaching of the blood withdrawal line of the extracorporeal blood circuit from the blood circuit of the patient.

For example, the "arterial disconnection" of the patient can include closing an arterial patient tube clamp which is arranged in an arterial line section or segment of the extracorporeal blood circuit and/or loosening or detaching of the arterial line section or segment of the extracorporeal blood circuit from the arterial branch of an access to the patient's vessel system.

The blood withdrawal line of the extracorporeal blood circuit or the tube system, respectively, can be connected to a saline bag.

During blood return, a blood pump can pump the blood with a flow of less than or equal to 100 ml/min.

After the patient has been disconnected from the blood withdrawal line and the patient tube clamps of the blood withdrawal line and the blood return line have been opened, the blood present in the extracorporeal blood circuit can be returned into the patient or into the blood circuit of the patient, respectively, via the blood return line being, e.g., an arterial or a venous connection needle depending on the blood treatment method.

In a further preferred embodiment of the method according to the present invention, the method comprises initiating the interruption of the blood treatment with the control device inducing or effecting at least one of the following processes: stopping a blood pump, closing a patient tube clamp of a blood withdrawal line and closing a patient tube clamp of a blood return line of an extracorporeal blood circuit, stopping an addition or administration of heparin (in form of a bolus or in form of a continuous administration), stopping a (continuous) addition or administration of an anti-coagulating agent, in particular citrate, terminating a balancing and/or stopping an administration of substitute.

The control device can induce or effect one, some, or all of the processes mentioned above.

Therefore, the control device can be designed and provided to control or activate corresponding conveying or pump devices, valve devices, flow rate devices and the like and/or to advise a user of performing or initiating a process step.

The control device can be designed and provided or configured to induce or effect all of the processes mentioned above at the same time.

The term "balancing" as used herein relates to components supplied to the extracorporeal blood and to components extracted therefrom.

Examples include infusions, albumins, blood concentrates, blood replacement concentrates such as the administration of substitute, medicaments such as anti-coagulating agents like heparin, the administration of citrate, calcium and the like as well as every other kind of fluid volume.

The term "administration of substitute" as used herein refers to the application or administration, respectively, of at least one substitute liquid into the patient's extracorporeal blood circuit. Suitable substitute liquids for infusion include, e.g., isotonic saline solutions such as 0.9%-NaCl solution.

The method according to the present invention can comprise connecting a blood withdrawal line of the extracorporeal blood circuit with a source of substituate.

In a further preferred embodiment, the method comprises disconnecting the blood return line of the extracorporeal blood circuit from the blood circuit of the patient, connecting the blood return line of the extracorporeal blood circuit with the source of substituate and circulating at least one substituate liquid through at least one section or segment of the extracorporeal blood circuit.

Following the disconnection of the blood return line, the patient can now substantially or completely be separated from the extracorporeal blood circuit.

The temporary interruption of a blood treatment session with the additional disconnection of a patient can preferably be used, for example, during an ECCT therapy (extracorporeal critical care therapy), CRRT (continuous renal replacement therapy), TA (therapeutical apheresis) and, liver replacement therapy, in different situations.

The temporary interruption permits the patient to be sent to short lasting, additional medical examinations and/or therapies; it also permits the position of the catheter to be checked, the placement of a new catheter, a check for the presence of an access problem (such as a problem with the access to the blood circuit of a patient), a visit to the bathroom or the like.

The method according to the present invention for temporarily interrupting the extracorporeal blood treatment can advantageously contribute to interrupting a blood treatment session without having to terminate the blood treatment completely and therewith having to discard, for example, the entire tube system of the extracorporeal blood circuit.

Once the patient has been disconnected from the extracorporeal blood circuit completely, the circulation of substituate liquid can advantageously be used for keeping the extracorporeal blood circuit prepared or primed for continuing the blood treatment session.

For means of circulating the substituate liquid through the extracorporeal blood circuit, conditions can be set or predetermined, respectively, which differ from the conditions and/or parameters set for the blood treatment session. For example, a reduced delivery or pump rate and/or a conveyance velocity of the blood pump can be set.

It can be possible to give information about the current process proceedings and/or about the duration of the current blood treatment session to a user. For example, the user can obtain a message on a screen or the like which can offer him the possibility to terminate the current blood treatment interruption at any time. The termination of the circulation can be initiated by means of a suited input device such as, for example, a stop hard key, and/or by means of an information window.

It can also be possible to change parameters—such as, e.g., pressure—and threshold windows of this parameter, as compared to the blood treatment session. Threshold windows can be deactivated. End of scales, i.e., for example, an upper threshold or an upper range of thresholds and/or a lower threshold or a lower range of thresholds, can be deactivated. For example, a lower venous end of scale can be deactivated. Likewise or additionally, it can be possible to deactivate an upper arterial end of scale. By this means, a monitoring of parameters relevant for the treatment can be stopped during the circulation correspondingly. This way, it can advantageously be possible to avoid possible false-positive alerts during the circulation.

The circulation can be terminated if, e.g., a detection device for detecting a composition of the line content of the extracorporeal blood circuit such as, for example, an optical detector, detects a particular, for example, a predetermined or preset optical density "OD dark". The blood treatment or the blood treatment session, respectively, can be continued.

If, for example, a duration of a circulation which had at first been determined as a maximum duration—here exemplarily given as, e.g., 4*h*— is exceeded (or at an earlier point in due time), a message can be output. The blood pump can be stopped.

Subsequently, the message may be confirmed (e.g. by a user) and the blood treatment or the circulation, respectively, may remain interrupted beyond the duration of circulation originally determined as a maximum duration.

In a preferred embodiment, the method according to the present invention comprises activating or controlling the control device in order to have the blood treatment session continued for the patient who has been reconnected to the blood treatment apparatus.

The connection of the patient can be, but does not have to be, part of the method according to the present invention.

The term "continue the blood treatment session" as used herein refers to a continuation or sequel of the blood treatment session.

The blood treatment session can be continued with the same parameters and/or under the same conditions as set at the beginning of the blood treatment session and/or during the course of the blood treatment session before interrupting it.

The control device can be activated or controlled by means of actuating such as pushing, rotating, switching etc. only one actuation device, optionally several actuation devices as well, in order to effect or induce a continuation or continuance of the blood treatment session of the patient who has been reconnected to the blood treatment apparatus following the temporary interruption thereof.

For continuing the blood treatment session, an arterial and venous connection of the patient, e.g., the connection of the blood withdrawal line and the blood return line of the extracorporeal blood circuit, to the blood circuit of the patient, starting the blood pump and conveying a line content inside the extracorporeal blood circuit until an optical density (OD) of the line content reaches a predetermined "OD dark", stopping the blood pump; and closing both patient tube clamps of the blood withdrawal line and the blood return line can be carried out.

The processes mentioned above can be initiated or triggered by the control device.

The object of the present invention is further achieved by a control device. All advantages achievable by means of the method according to the present invention can likewise undiminishedly be achieved by the control device according to the present invention.

The control device of the present invention is provided and configured to be activated or controlled in order to temporarily interrupt the blood treatment being effected by means of a blood treatment apparatus.

The interruption of the blood treatment session can be performed with the intention to continue the extracorporeal blood treatment.

The control device according to the present invention can be provided and configured to be used for temporarily interrupting the blood treatment apparatus in a method of the present invention.

The control device can be provided and configured to be activated or controlled by means of actuating only one actuation device of the user.

The control device can be provided and configured to induce or effect that the blood treatment session is continued.

The control device can, for example, be provided and configured to induce or effect the blood treatment session of the patient to be continued following the temporary interruption thereof by the user actuating only one actuation device.

The object of the present invention is further achieved by a blood treatment apparatus. All advantages achievable by means of the method according to the present invention can likewise undiminishedly be achieved by the blood treatment apparatus according to the present invention.

The blood treatment apparatus according to the present invention is suited and/or provided or configured, respectively, for an extracorporeal blood treatment such as, for example, dialysis, hemofiltration, hemodiafiltration, a method of gassing blood, apheresis, adsorption and the like.

The blood treatment apparatus comprises at least one control device according to the present invention.

Furthermore, the blood treatment apparatus can comprise further devices such as input and/or output devices, storage means and the like and/or can be connected to such devices.

The blood treatment apparatus can in particular comprise at least one actuation device. The actuation device can be provided and configured in order to enable that an activation or a control of the control device is effected. Such a control or activation can, for example, be achieved or triggered, respectively, by a single or one-time actuation of the actuation device.

The object of the present invention is further achieved by a digital storage means and/or a computer program product and/or a computer program. All advantages achievable by means of the method of the present invention can likewise undiminishedly be achieved by the digital storage means according to the present invention, the computer program product according to the present invention and/or the computer program according to the present invention.

The digital storage means, which is in particular a disc, CD or DVD, preferably features electrically readable control signals which are able to interact with a programmable computer system such that the technical or automatically performable steps of the method according to the present invention will be executed.

Thereby, all, a few or some of the automatically performed steps of the method according to the present invention can be induced. The latter also applies for the computer program product and the computer program.

The computer program product preferably comprises a program code stored on a machine readable medium for executing the technical or automatically permeable steps of a method according to the present invention when the program product is being executed on a computer.

The term "machine readable data medium' as used herein refers to a medium containing data or information being interpretable by software and/or hardware. The medium can be a data medium like a disc, a CD, DVD and the like.

The computer program comprises a program code for executing the technical or automatically performable steps of the method according to the present invention when the program is being executed on a computer.

The present invention can advantageously enable a simpler interruption of a blood treatment session.

By means of the control device, it can thereby advantageously be possible to trigger or effect or induce, respectively, and/or perform several operations at the same time. The present invention can thus advantageously provide a simplification of the interruption of a blood treatment session. Furthermore, by virtue of the present invention, since several steps can virtually be induced or effected simultaneously, time can be saved. Additionally, due to their initiation by means of the control device according to the present invention, subsequent steps can be adapted to each other optimally.

The mere interruption of the blood treatment session in case of need can be of advantage as compared to a termination or a complete stop, respectively, of the blood treatment session. On the one hand, it can advantageously contribute to save costs for the client and/or the patient. For example, the tube system for CRRT blood treatments can be used up to 72 h and can advantageously also be used again following a short time blood treatment interruption until a maximum time blood treatment of 72 h is reached.

Planning the patient's examinations of a certain day and/or of further blood treatments can advantageously be take place, independently from the blood treatment session.

The present invention can advantageously provide a high user friendliness. Possible, manually accomplished steps can be reduced to a great extent or can even be ceased completely. Moreover, it can advantageously be possible to perform a simultaneous change of parameters which are present at or in the blood treatment apparatus or in the extracorporeal blood circuit, in a concerted manner. The adaptation of parameters such as, for example, a reduction of the blood flow and the like, can advantageously also be performed in an automated manner, depending from further parameters resulting from preparing for the interruption.

As the control device can be equipped with or connected to devices for displaying and/or outputting notifications and the like, a user can advantageously be informed about all or substantially all operation steps and/or can be correspondingly led through the currently performed process (step). Feedbacks between sensors which report results of measurements of the parameters involved in the interruption are thereby possible, and they are provided for in certain embodiments.

The present invention can advantageously provide for a higher security of the whole system. It can thus, for example, advantageously be possible to monitor and/or display the reinfusion volume during the current reinfusion. A maximum reinfusion volume can be monitored. If the maximum reinfusion volume is about to be exceeded, a respective message could advantageously be output, and the reinfusion process could possibly be stopped completely.

By monitoring the maximum duration of a blood treatment interruption, it can further be possible to provide a higher security of the whole system.

BRIEF DESCRIPTION OF THE DRAWINGS

The present invention is in the following illustrated by way of example with reference to the appended drawings, wherein.

DETAILED DESCRIPTION OF THE DRAWINGS

As stated above, there are extracorporeal blood treatment methods in which the blood withdrawal line of an extracorporeal blood circuit is the arterial line section or segment of the extracorporeal blood circuit and in which the blood return line is the venous line section or segment correspondingly. Examples thereof include blood treatment methods such as extracorporeal blood purification methods, e.g., hemodialysis, hemofiltration, hemodiafiltration and the like.

In other extracorporeal blood treatment methods, e.g., methods of enriching blood with oxygen, the direction of withdrawal can be reversed as compared to the direction of withdrawal of, e.g., a hemodialysis, such that blood is withdrawn via the blood withdrawal line from the venous leg of the patient's vascular system and, following its enrichment with oxygen, is returned via the blood return line into the arterial leg of the patient's vascular system.

In the following embodiments, the present invention is exemplarily illustrated by way of an arterial blood withdrawal line and a venous blood return line. However, as a person skilled in the art will easily recognize, the directions or points of withdrawal and return do not have any influence on the practicability of the method according to the present invention.

The method shall not be limited to the said embodiment.

Figure 1:
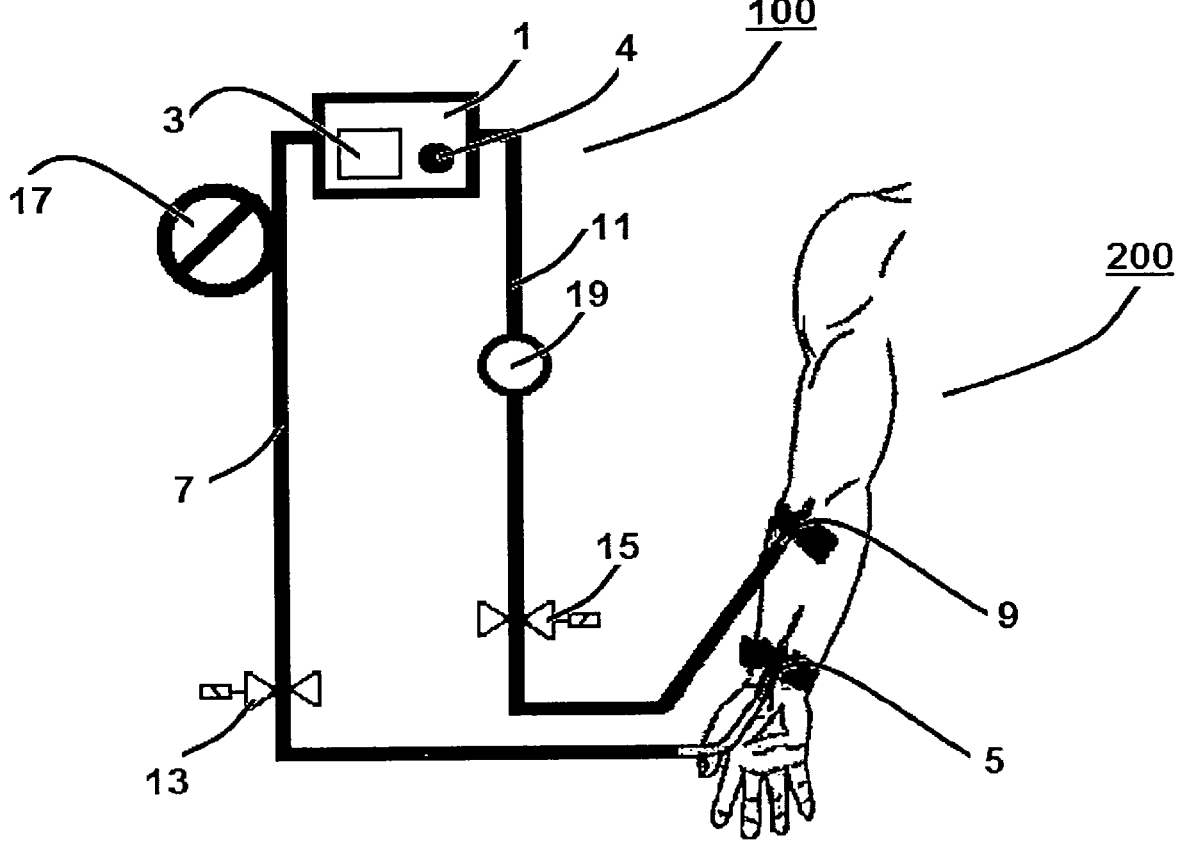
FIG. 1 shows a schematic overview of an exemplary arrangement for performing the method according to the present invention.

FIG. 1 shows a schematic overview of an arrangement for performing a blood treatment session.

FIG. 1 shows an extracorporeal blood circuit 100 which is connected to a blood treatment apparatus 1 according to the present invention. The blood treatment apparatus 1 comprises a control device 3 and an actuation device 4.

A patient 200 is connected to the extracorporeal blood circuit 100 via a patient access. More precisely, the patient 200 is connected to a blood withdrawal line, here an arterial line section 7, of the extracorporeal circuit 100 via a first patient access, here an arterial patient access 5. The patient 200 is connected to a blood return line, here a venous line section 11, of the extracorporeal blood circuit 100 via a second patient access, here a venous patient access 9.

In the arterial line section 7, a first patient tube clamp, here an arterial patient tube clamp 13, is arranged. In the venous line section 11, a second patient tube clamp, here a venous patient tube clamp 15, is arranged.

FIG. 1 shows the arterial patient tube clamp 13 and the venous patient tube clamp 15 in an opened state.

By means of a blood pump 17, blood of the patient 200 is conveyed within the extracorporeal blood circuit 100.

A detection device, e.g., an optical detector 19 is provided in the venous line section 11, which can be designed and provided to detect an optical density (OD) of a line content present in the interior of the extracorporeal blood circuit 100.

Figure 2:
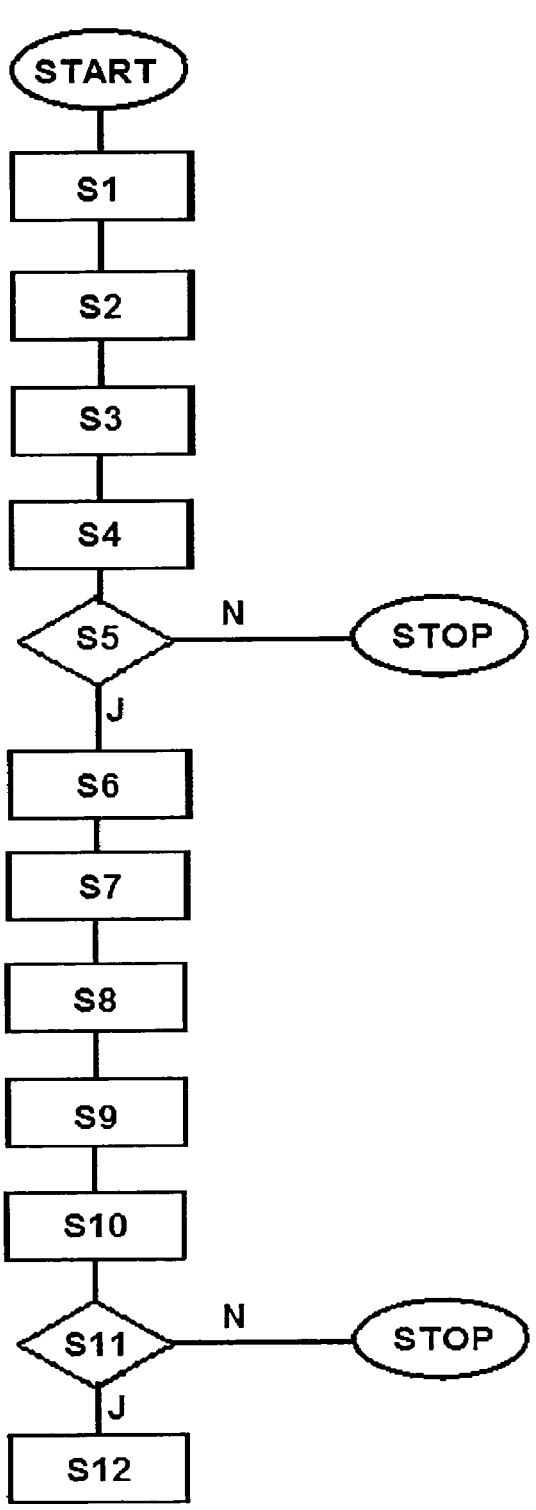
FIG. 2 shows a flow diagram of a method according to the present invention.

FIG. 2 schematically shows a flow diagram of a method according to the present invention for temporarily interrupting an extracorporeal blood treatment of a patient.

For easier understanding the co-operation of the single components, reference is made to the arrangement shown in FIG. 1. The components involved in the method according to the present invention are for this reason denoted with the reference numerals of FIG. 1 though they are not necessarily shown in FIG. 2, too.

At first, a user can select a soft key "blood treatment interruption" in a menu (not shown in FIG. 2).

In the present case, in step S1, the user selects the blood treatment interruption with blood return. The selection can be performed by—preferably only one time actuating—an actuation device 4 such as a soft key. The soft key can be arranged on a screen (not shown) of the blood treatment apparatus 1. The actuation can, however, also be carried out in any other way known to a person skilled in the art.

In subsequent step S2, the control device 3 induces or effects the stop of the blood pump 17 of the extracorporeal blood circuit 100.

Thereby, an arterial patient tube clamp 13 and/or a venous patient tube clamp 15 can be closed.

The control device 3 can further induce or effect the stop of a heparin bolus, the stop of continuous anti-coagulation additives such as heparin, citrate, Ci-Ca (citrate-calcium) with Ca being the antagonist of the anti-coagulation, the termination of a balancing and/or the stop of a substitute bolus.

On the screen of the blood treatment apparatus 1, instructions for the further proceedings and/or information about the current process step can be displayed.

For example, a user can be notified that the patient 200 has to be disconnected arterially. In step S3, the user can be requested to disconnect the patient 200.

The arterial line section 7 of the tube system of the extracorporeal blood circuit 100 is then preferably connected to a source of substitute such as a saline bag.

Before starting the reinfusion, all connections can be checked for their tightness.

The continuous anti-coagulation additions can further be maintained in a ceased state. The balancing can also further be maintained in a ceased state.

In step S4, the reinfusion can be started by the control device 3 inducing or effecting the reinfusion—preferably by means of actuating again another soft key.

For performing the reinfusion, the arterial patient tube clamp 13 and the venous patient tube clamp 15 can be opened. The blood pump 17 can be started. The blood pump 17 can, for example, be operated with a conveyance velocity of 100 ml/min.

A blood flow of 100 ml/min can, for example, indicate that the blood flow during the reinfusion has to be reduced—as compared to the blood flow during the blood treatment session. If the blood flow has already been <100 ml/min during the blood treatment session, then the conveyance velocity of the blood pump 17 can be maintained (on this lower value below 100 ml). However, according to the present invention, also velocities above 100 ml/min are possible for the reinfusion.

Instructions for the further proceedings and/or information about the current process step for the user can be displayed again on the screen of the blood treatment apparatus 1.

Further background processes and/or monitoring processes can take place. These processes can be different from the processes performed during a blood treatment session.

In step S5, there can be requested if a detection device such as an optical detector 19 detects if an optical density with the target value "OD bright" is present inside a predetermined volume.

The presence of the value for "OD bright" can indicate that there is substantially no blood in a line content inside the extracorporeal blood circuit 100 anymore. The value "OD bright" can be a predetermined value. It can, e.g., be deposited internally in a storage means and/or a software.

If the value "OD bright" has not been reached ("N" for "NO"), a message can be output. The blood pump 17 can be stopped in each case.

If the predetermined value for "OD bright" has been reached ("J" for "YES"), in step S6, a stop of the blood pump 17 can be induced or effected by means of the control device 3.

The arterial patient tube clamp 13 and the venous patient tube clamp 15 are closed.

The patient 200 can be disconnected venously. The patient 200 is now completely separated from the blood treatment apparatus 1 and can, for example, leave the treatment room.

In step S7, a circulation of substitute liquid by means of the control device 3 can be effected or induced.

At first, the screen of the blood treatment apparatus 1 can display a message including a request about if the patient has been disconnected.

If the patient 200 has been disconnected completely from the blood treatment apparatus 1 or parts thereof, respectively, such as the extracorporeal blood circuit 100, instructions for further proceedings and information about the current process can be displayed on the screen.

Next, it is also intended to connect the venous line section 11 to the source of substitute, e.g., the saline bag. This can be carried out by the user.

All connections can be checked for their tightness.

Then, in step S8, the control device 3 can effect or induce the circulation of the substitute liquid. This can advantageously be achieved again by merely actuating a soft key.

The continuous anti-coagulation can further be maintained ceased or stopped. The balancing can further be maintained stopped.

The blood pump 17 can furthermore be operated with a conveyance velocity of 100 ml/min.

Instructions for further proceedings and/or information about the current process step and/or about the duration of the current blood treatment interruption can be displayed on the screen.

At this point, the user can—for example, by means of a message or an information on the screen—get the possibility to terminate the current blood treatment interruption (at any point of time).

Further background processes and/or monitoring processes can take place. These process proceedings can differ from process proceedings during the blood treatment session.

For example, other threshold windows, e.g. of the pressure, can be set which differ from threshold windows during the blood treatment. Threshold windows can be deactivated. A lower venous end of scale can be deactivated. An upper arterial end of scale can be deactivated.

The circulation can, for example, stop if an optical density "OD dark" is detected, wherein "OD dark" can also be a value which has been deposited in a storage means. The blood treatment session can be continued.

In a case in which a duration of the circulation which had originally been set to a maximum of 4 h is exceeded, a corresponding message can be output. The blood pump 17 can be stopped. This message can be affirmed and the blood treatment interruption or the circulation, respectively, can be continued.

If the blood treatment session shall be continued, the control device 3 can be effect or induce a termination of the circulation of substitute liquid in step S9.

At first, the blood pump 17 which has conveyed substitute liquid during the circulation can be stopped.

The arterial patient tube clamp 13 and the venous patient tube clamp 15 can be closed.

The screen can again display instructions for further proceedings and/or information about the current process step. These can include a hint with instructions for the connection of the patient.

Furthermore, the control device can induce or effect the start of the blood pump 17 by means of, for example, actuating a soft key.

Preferably, the arterial connection of the patient is affirmed. Subsequently, the control device 3 can be activated or controlled, for example, by merely pushing a key, such that the blood pump 17 is started. The blood pump 17 can further convey with a blood flow of ≤100 ml/min.

The arterial patient tube clamp 13 and the venous patient tube clamp 15 can be opened again.

The screen can again display instructions for further proceedings and/or information about the current process step.

Moreover, several background processes and/or monitoring processes can take place again.

In step S10, the connection of the patient will be started at first.

In step S11, it is requested if a particular (predetermined) optical density "OD dark" has been reached inside a predetermined volume. The value of the optical density "OD dark" can have been deposited in a storage means and/or in a software.

If the value for "OD dark" has not been reached, a corresponding message can be output and the blood pump 17 can be stopped.

If the value for "OD dark" has been reached, blood pump 17 is stopped.

Then, the arterial patient tube clamp 13 and the venous patient tube clamp 15 can be closed.

As soon as the patient 200 (for example, following another blood treatment) is available again, the procedure can be performed in reverse order such that the blood treatment session can be continued.

In order to continue the blood treatment, in step S12, the control device 3 can induce or effect a restart of the blood pump 17 with the blood flow that had been present before the blood treatment interruption has been started.

The arterial patient tube clamp 13 and the venous patient tube clamp 15 can be opened again.

The continuous anti-coagulation addition (heparin, citrate, Ci-Ca, calcium as anti-coagulating agent) and the balancing can be restarted.

All monitoring processes of the blood treatment session can be reactivated.

What is claimed is:

1. A method for temporarily interrupting an extracorporeal blood treatment of a patient who is connected to a blood treatment apparatus for the extracorporeal blood treatment, the method comprising:

connecting an extracorporeal blood circuit to the patient, the extracorporeal blood circuit connected to the blood treatment apparatus and comprising:

a blood withdrawal line connected to the patient; and a blood return line connected to the patient;

activating or controlling a control device of the blood treatment apparatus to start the extracorporeal blood treatment, the extracorporeal blood treatment comprising running a blood pump to: (i) withdraw blood from the patient; (ii) convey the blood through the extracorporeal blood circuit; and (iii) return the blood to the patient, the control device configured to bring the blood treatment apparatus into a temporary interruption state in which a session of the extracorporeal blood treatment can be interrupted temporarily to, at a later time, continue the session of the extracorporeal blood treatment;

during the extracorporeal blood treatment, activating or controlling the control device to bring the blood treatment apparatus into the temporary interruption state, wherein, during the temporary interruption state, blood from the blood withdrawal line is conveyed by the blood pump to perform a reinfusion of the blood from the blood withdrawal line to the patient;

after stopping the blood pump, disconnecting the patient from the extracorporeal blood circuit, and then circulating at least one substitute liquid through at least one section of the extracorporeal blood circuit while the patient is disconnected from the extracorporeal blood circuit during the temporary interruption state;

after the stopping of the blood pump, receiving a notification generated by the control device in response to the stopping of the blood pump, the notification comprising a request to the patient or a user of the control device to confirm if the patient has been disconnected from the extracorporeal blood circuit;

confirming that the patient has been disconnected from the extracorporeal blood circuit;

in response to confirming, receiving one or more messages, generated by the control device at respective steps of the temporary interruption of the session of the extracorporeal blood treatment, to inform the patient or the user of the control device about a next operation step of the temporary interruption;

reconnecting the patient to the extracorporeal blood circuit; and after the reconnecting, activating or controlling the control device to continue the session of the extracorporeal blood treatment using the blood treatment apparatus.

2. The method according to claim 1, wherein the control device is activated or controlled by actuating only one actuation device to bring the blood treatment apparatus into the temporary interruption state.

3. The method according to claim 1, further comprising initiating the temporary interruption of the session of the extracorporeal blood treatment, by inducing or effecting by use of the control device, at least one process selected from the group consisting of:

closing a patient tube clamp of the blood withdrawal line and closing a patient tube clamp of the blood return line of the extracorporeal blood circuit;

stopping an administration of heparin;

stopping administration of an anti-coagulating agent;

terminating a balancing; and stopping an addition or administration of substitute liquid.

4. The method according to claim 1, wherein disconnecting the patient from the extracorporeal blood circuit includes disconnecting the blood return line of the extracorporeal blood circuit from a blood circuit of the patient; and the method further comprises:

connecting the blood return line of the extracorporeal blood circuit with a source of substitute liquid.

5. The method according to claim 1, wherein the control device is activated or controlled by actuating only one actuation device to induce or effect the continuation of the session of the extracorporeal blood treatment.

6. The method according to claim 5, wherein the actuation or activation or control of the control device comprises pushing, rotating, or switching the actuation device.

7. The method according to claim 5, wherein the actuation device includes a knob, a key, a soft key, a hard key, a switch, a controller, a button of a touch pad, or a button of a touch screen.

8. The method according to claim 1, further comprising performing the temporary interruption to, at the later time, continue the session of the extracorporeal blood treatment by means of at least one medical device used for the extracorporeal blood treatment prior to the temporary interruption of the session of the extracorporeal blood treatment.

9. The method according to claim 1, wherein by means of activating or controlling the control device, a background process assisting the patient or the user in different stages of the temporary interruption of the session of the extracorporeal blood treatment is initiated automatically.

10. The method according to claim 1, wherein the control device is configured to generate visual or acoustic notifications.

11. The method according to claim 10, wherein the control device is configured to control or activate corresponding conveying or pump devices, valve devices, flow rate devices and/or to advise the patient or the user of performing or initiating a step.

12. The method according to claim 1, further comprising permitting the patient or the user to check a position of a catheter and/or to place a new catheter.

13. The method according to claim 1, further comprising interrupting the session of the extracorporeal blood treatment without terminating the session of the extracorporeal blood treatment completely.

14. The method according to claim 1, wherein the session of the extracorporeal blood treatment is resumed after the temporary interruption with the same parameters used before the session of the extracorporeal blood treatment was interrupted.

15. A system configured to effect the temporary interruption state of the blood treatment apparatus by performing operations in the method according to claim 1, the system comprising the control device.

16. The system according to claim 15, wherein the control device is configured to be activated or controlled by actuating only one actuation device.

17. The system according to claim 15, wherein the control device is configured to induce or effect a continuation of the session of the extracorporeal blood treatment.

18. The system according to claim 15, wherein the control device is part of the blood treatment apparatus for the extracorporeal blood treatment.

19. The system according to claim 18, wherein the blood treatment apparatus further comprises at least one actuation device which by itself is configured to activate or control the control device.

20. A non-transitory computer-readable storage medium with an executable program stored thereon, wherein the program instructs a programmable computer system to execute operations of the method according to claim 1.

* * * * *